US00PP35853P2

(12) United States Plant Patent
Lucas

(10) Patent No.: US PP35,853 P2
(45) Date of Patent: Jun. 4, 2024

(54) LOROPETALUM PLANT NAMED 'PURLOROCHA'

(50) Latin Name: *Loropetalum chinense*
Varietal Denomination: Purlorocha

(71) Applicant: William Lucas, Semmes, AL (US)

(72) Inventor: William Lucas, Semmes, AL (US)

(73) Assignee: Yuji Suzuki, Kawaguchi (JP)

( * ) Notice: Subject to any disclaimer, the term of this patent is extended or adjusted under 35 U.S.C. 154(b) by 0 days.

(21) Appl. No.: 18/236,028

(22) Filed: Aug. 21, 2023

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP23,176 P2 11/2012 Suzuki

*Primary Examiner* — Susan McCormick Ewoldt
(74) *Attorney, Agent, or Firm* — Panitch Schwarze Belisario & Nadel LLP; Stephany G. Small; Travis W. Bliss

(57) ABSTRACT

A new and distinct cultivar of *Loropetalum* plant, referred to by its cultivar name, 'Purlorocha', is disclosed. The new cultivar is characterized by its deep purplish, red-colored flowers and it is also characterized by its dark, burgundy-colored foliage. The new cultivar provides a moderately vigorous, compact, and mounded, well-branched growth habit.

2 Drawing Sheets

Figure 1:
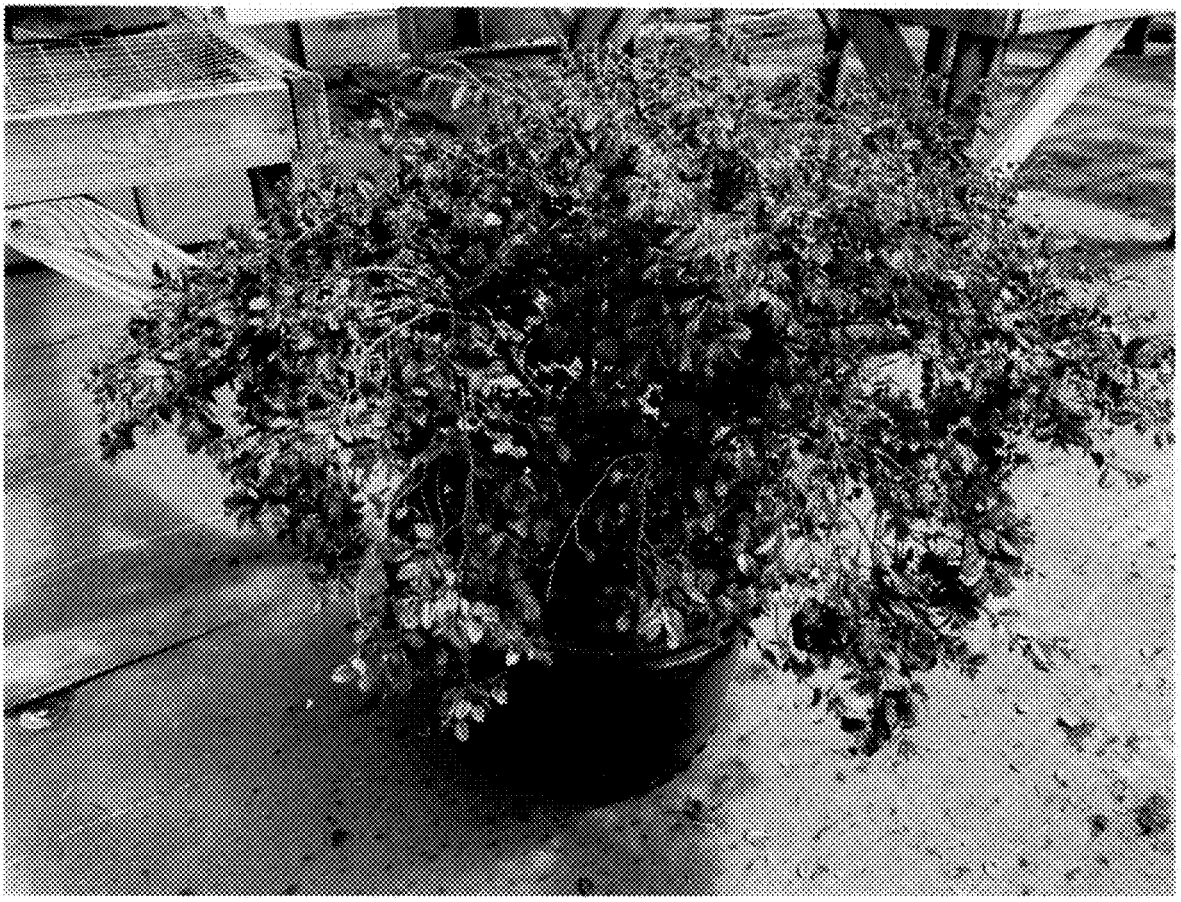

Latin name of genus and species of plant claimed: *Loropetalum chinense.*

Variety denomination: 'Purlorocha'.

STATEMENT REGARDING PRIOR DISCLOSURES BY THE INVENTOR

The first offer for sale of the new variety was Aug. 22, 2022, in the United States of America. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The present invention relates to a new and distinct cultivar of *Loropetalum* plant botanically known as *Loropetalum chinense* and hereinafter referred to by the cultivar name 'Purlorocha'.

The new cultivar originated as a naturally occurring branch mutation of *Loropetalum* 'Kurobijin' (U.S. Plant Pat. No. 23,176) at Wilmer, Alabama in June 2020. The new *Loropetalum* plant was discovered and selected by the Inventor on a single plant from within a production block of 'Kurobijin' in a controlled nursery environment.

The new variety has been found to undergo asexual propagation in Wilmer, Alabama by terminal stem cuttings since June 2021. Asexual propagation has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Purlorocha' as a new and distinct cultivar of *Loropetalum* plant:

(a) Deep purplish, red-colored flowers,
(b) Dark, burgundy-colored foliage, and
(c) Moderately vigorous, compact, and mounded, well-branched growth habit.

The new variety of the present invention can be readily distinguished from its ancestor. More specifically, plants of the new cultivar differ from plants of the 'Kurobijin' variety (i.e., the parent variety). For example, plants of the new cultivar have a more compact and dense growth habit compared to plants of 'Kurobijin' and plants of the new cultivar produce flowers which are more purple in color compared to the flowers produced by plants of 'Kurobijin', which are more red in color.

Moreover, the new cultivar can be readily distinguished from other similar non-parental varieties. Of the many commercially available *Loropetalum* cultivars, one of the most similar non-parental variety in comparison to the new cultivar is 'Hines Dark Leaf' (not patented). However, in comparison, plants of the new cultivar differ from plants of 'Hines Dark Leaf' in at least because plants of 'Hines Dark Leaf' produces flowers which are lighter in color compared to flowers produced by the new variety.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Purlorocha'. The illustrated plant was approximately two years of age and was grown in a seven-gallon pot during April 2023, in a nursery setting in Cochranville, Pennsylvania.

FIG. 1—illustrates a side view of the overall growth and flowering habit of 'Purlorocha'.

Figure 2:
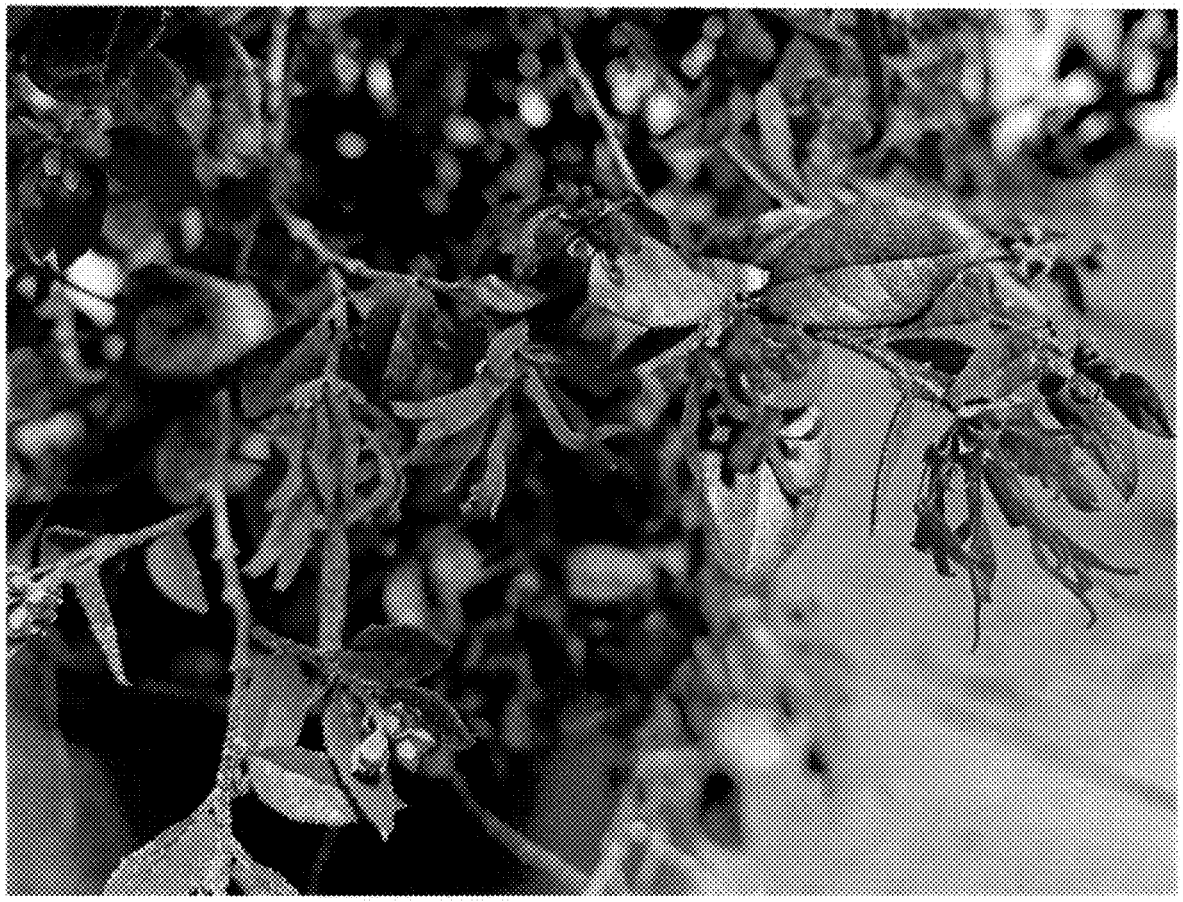

FIG. 2—illustrates a close-up view of an inflorescence and sepals of 'Purlorocha'.

DETAILED BOTANICAL DESCRIPTION

The chart used in the identification of colors described herein is The R.H.S. Colour Chart of The Royal Horticultural Society, London, England, 2015 edition, except where general color terms of ordinary significance are used. The R.H.S. Colour Chart designation used herein represents the closest color observed on the majority of the specified botanical feature. The flower color values were determined in April 2023, and the foliage and other color values were determined in June 2023, under natural light conditions in Cochranville, Pennsylvania.

The following descriptions and measurements represent averages of a typical plant, which was produced from cuttings from stock plants and grown in seven-gallon containers for approximately two years in an outdoor nursery in Cochranville, PA.

Botanical classification: *Loropetalum chinense* cultivar 'Purlorocha'.

Parentage: Naturally occurring branch mutation of 'Kurobijin'.

Propagation:

*Type cutting*.—Terminal stem.

*Time to initiate roots*.—Approximately 30 days.

*Time to produce a rooted cutting*.—Approximately 120 days.

*Root description*.—Fibrous.

*Rooting habit*.—Freely branching.

Plant description:

*Commercial crop time*.—Approximately 180 days from a rooted cutting to finish in a one-gallon container.

*Growth habit and general appearance*.—Moderate growth vigor, and compact, mounded and well-branched growth habit.

*Size*.—Height from soil level to top of plant plane: Approximately 55.0 cm. Width: Approximately 92.0 cm.

*Branching habit*.—Freely branching, pinching enhances basal branching. Quantity of main branches per plant: Approximately 3.

*Branch*.—Strength: Strong, somewhat flexible, becomes woody with age. Length of main branch: Approximately 32.0 cm. Diameter of main branch: Approximately 8.0 mm. Length of lateral branch: Approximately 14.0 cm. Diameter of lateral branch: Approximately 3.0 mm. Length of central internode: Approximately 1.0 cm. Texture: Viscid, densely glandular pubescent. Color of young stems: Brown Group 200B. Color of mature stems: Brown Group N200B.

Foliage description:

*General description*.—Quantity of leaves per unbranched lateral stem: Approximately 12. Quantity of leaves per branched lateral stem: 186. Form: Simple. Arrangement: Alternate. Durability to stress: Moderate to high.

*Leaves*.—Shape: Oval. Margin: Entire with stellate hairs. Apex: Acute to obtuse. Base: Rounded to cuneate, occasionally asymmetrical. Venation pattern: Pinnate. Length of mature leaf: Approximately 3.0 cm. Width of mature leaf: Approximately 1.8 cm. Texture of upper surface: Firm to leathery, with impressed veins. Texture of lower surface: Mildly rough. Color of upper surface of young foliage: Greyed-Purple Group N187A with indistinguishable venation. Color of lower surface of young foliage: Purple Group N79B with indistinguishable venation. Color of upper surface of mature foliage: Black Group 202A with indistinguishable venation. Color of lower surface of mature foliage: Violet-Blue Group N92A with indistinguishable venation.

*Petiole*.—Shape: Rounded, slightly curved. Length: Approximately 2.0 mm. Width: Approximately 1.0 mm. Color: Brown Group 200B.

Flowering description:

*Flowering*.—April into early May in Cochranville, PA.

*Lastingness of flower on the plant*.—Approximately 2 to 3 weeks.

Inflorescence description:

*General description*.—Type: Terminal raceme, occasionally solitary at terminals or leaf axils. Fragrance: None. Height: Approximately 1.7 cm. Width: Approximately 2.5 cm. Quantity of flowers and buds per inflorescence. Approximately 5.

Flower description:

*General description*.—Form: Perfect, strap-like. Aspect: Outward to slightly drooping.

*Bud*.—Shape: Rounded. Length: Approximately 2.0 mm. Diameter: Approximately 2.0 mm. Color: Purple Group N77B.

*Petals*.—Quantity: 4. Shape: Linear. Margin: Entire. Apex: Truncate. Base: Cuneate. Length: Approximately 1.0 cm. Width: Approximately 1.0 mm. Texture of upper and lower surfaces: Glabrous. Color of upper and under surfaces when first and fully open: A color between Red-Purple Group 71A and 71B.

*Sepals*.—Quantity: 4, fused on lower half. Length: Approximately 3.0 mm. Width: Approximately 2.0 mm. Texture of upper and lower surfaces: Glabrous. Color of upper surface of sepals: Red-Purple Group 59B. Color of lower surface of sepals: Red-Purple Group 59C.

*Pedicel*.—Strength: Strong. Aspect: Droops downwards. Length: Approximately 1.0 mm. Diameter: Approximately 0.5 mm. Texture: Glabrous to moderately pubescent. Color: Purple Group N77B.

*Reproductive organs*.—Androecium: Stamen quantity: 4 per flower. Anther length: Less than 1.0 mm. Filament Length: Less than 1.0 mm. Anther color: Red-Purple Group 61B. Pollen amount: None observed. Gynoecium: Pistil quantity: 2 per flower. Pistil length: Less than 1.0 mm. Stigma color: Red-Purple Group 60A. Style length: Less than 1.0 mm. Ovary color: Red-Purple Group 61B.

Seed and fruit production: Neither seed nor fruit production has been observed.

Disease and pest resistance: Resistance to pathogens and pests common to *Loropetalum* has not been observed.

Winter hardiness: Zone 7.

The new cultivar has not been observed under all possible environmental conditions to date. Accordingly, it is possible that the phenotype may vary somewhat with variations in the environment, such as temperature, light intensity, and day length, without, however, any variance in genotype.

I claim:

1. A new and distinct cultivar of *Loropetalum* plant named 'Purlorocha' characterized by the following combination of characteristics:

(a) forms deep purplish, red-colored flowers, (b) exhibits dark, burgundy-colored foliage and, (c) provides a moderately vigorous, compact, and mounded, well-branched growth habit;

substantially as herein illustrated and described.

* * * * *